US012727951B2

(12) United States Patent
Wang et al.

(10) Patent No.: US 12,727,951 B2
(45) Date of Patent: Sep. 8, 2026

(54) ROBOTIC BRONCHOSCOPY NAVIGATION METHOD AND SYSTEM

(71) Applicant: INDUSTRIAL TECHNOLOGY RESEARCH INSTITUTE, Hsinchu (TW)

(72) Inventors: An-Peng Wang, Kaohsiung City (TW); Chien-Yu Wu, Yunlin County (TW); Cheng-Peng Kuan, Zhubei City (TW); Shu Huang, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 494 days.

(21) Appl. No.: 18/071,450

(22) Filed: Nov. 29, 2022

(65) Prior Publication Data

US 2024/0074823 A1 Mar. 7, 2024

(30) Foreign Application Priority Data

Sep. 2, 2022 (TW) ................................. 111133314

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00149* (2013.01); *A61B 1/2676* (2013.01); (Continued)

(58) Field of Classification Search
CPC ... A61B 1/00149; A61B 1/267; A61B 1/2676; A61B 34/20; A61B 34/30; A61B 2034/2061; A61B 2034/2065
See application file for complete search history.

(56) References Cited

U.S. PATENT DOCUMENTS 7,930,065 B2 4/2011 Larkin et al.
8,801,601 B2 8/2014 Prisco et al.
(Continued)

FOREIGN PATENT DOCUMENTS

CN 104321007 B 11/2016
CN 104323860 B 8/2018
(Continued)

OTHER PUBLICATIONS

Taiwan Office Action dated Apr. 27, 2023 as received in application No. 111133314.
(Continued)

*Primary Examiner* — Alexandra L Newton
(74) *Attorney, Agent, or Firm* — Maschoff Brennan

(57) ABSTRACT

A robotic bronchoscopy navigation method, performed by a processing control device, includes: performing a navigation procedure according to obtained navigation image, the navigation procedure including: determining whether the navigation image has a node, if the navigation image does not have the node, controlling a bending part of a robotic bronchoscopy to move toward an image center of the navigation image, if the navigation image has the node, calculating a distance between the bronchoscopy and the node, controlling the bending part to move according to a default branch when the distance is smaller than a threshold of distance, and determining whether the default branch is a destination branch where a destination is located, if the default branch is not the destination branch, obtaining another navigation image, and performing the navigation procedure on the another navigation image, and if the default branch is the destination branch, outputting a notification.

5 Claims, 9 Drawing Sheets

(51) Int. Cl.
*A61B 1/267* (2006.01)
*A61B 34/20* (2016.01)

(52) U.S. Cl.
CPC ................. *A61B 2034/2055* (2016.02); *A61B 2034/2065* (2016.02); *A61B 2034/301* (2016.02); *A61B 2034/303* (2016.02)

(56) References Cited

U.S. PATENT DOCUMENTS

| | | | | |
|---|---|---|---|---|
| 9,125,679 | B2 | 9/2015 | Larkin et al. | |
| 10,555,778 | B2 | 2/2020 | Ummalaneni | |
| 2010/0249506 | A1* | 9/2010 | Prisco | A61B 1/0051 600/117 |
| 2012/0289777 | A1* | 11/2012 | Chopra | A61B 5/6852 382/128 |
| 2014/0180063 | A1* | 6/2014 | Zhao | A61B 1/2676 600/424 |
| 2020/0170720 | A1 | 6/2020 | Ummalaneni | |
| 2020/0261155 | A1 | 8/2020 | Popovic et al. | |
| 2021/0030476 | A1 | 2/2021 | Nakashima et al. | |
| 2022/0125527 | A1 | 4/2022 | Hsu et al. | |
| 2022/0233251 | A1* | 7/2022 | Bowling | A61B 34/35 |
| 2024/0252260 | A1* | 8/2024 | Liu | A61B 34/10 |

FOREIGN PATENT DOCUMENTS

| | | | |
|---|---|---|---|
| CN | 106725853 | B | 7/2019 |
| CN | 110832544 | A | 2/2020 |
| CN | 112741689 | A | 5/2021 |
| CN | 114305680 | A | 4/2022 |
| EP | 3 178 435 | B1 | 9/2019 |
| WO | 2015/061756 | A1 | 4/2015 |
| WO | 2016/093848 | A1 | 6/2016 |

OTHER PUBLICATIONS

Lee Danisch, et al., "Spatially continuous six degree of freedom position and orientation sensor," Sensor Review, vol. 19, Issue 2, pp. 106-112 (Jun. 1999).

Xiongbiao Luo, et al., "Advanced Endoscopic Navigation: Surgical Big Data, Methodology, and Applications," Annual Review of Biomedical Engineering, vol. 20, pp. 221-251 (Jun. 2018).

Samuel Victor Kemp, "Navigation Bronchoscopy," Respiration, vol. 99, Issue 4, pp. 277-286 (Apr. 2020).

Murilo M. Marinho, et al., "Virtual Fixture Assistance for Suturing in Robot-Aided Pediatric Endoscopic Surgery," IEEE Robotics and Automation Letters, vol. 5, Issue 2, pp. 524-531 (Apr. 2020).

Abhinav Agrawal, et al., "Robotic bronchoscopy for pulmonary lesions: a review of existingtechnologies and clinical data," Journal of Thoracic Disease, vol. 12, Issue 6, pp. 3279-3286 (Jun. 2020).

Mohan Giri, et al., "Virtual bronchoscopic navigation versus non-virtual bronchoscopic navigationassisted bronchoscopy for the diagnosis of peripheral pulmonary lesions: a systematic review and meta-analysis," Therapeutic Advances in Respiratory Disease, vol. 15, pp. 1-11 (Jan. 2021).

Alexander C. Chen, MD, et al., "Robotic Bronchoscopy for Peripheral Pulmonary Lesions," Chest, vol. 159, Issue 2, pp. 845-852 (Feb. 2021).

Zuoming Fu, et al., "The Future of Endoscopic Navigation: A Review of Advanced Endoscopic Vision Technology," IEEE Access, vol. 9, pp. 41144-41167 (Mar. 10, 2021).

Artur Banach, "Visual Navigation in Minimally Invasive Surgery," Queensland University of Technology, pp. 1-92 (Feb. 11, 2022).

Caspar Gruijthuijsen, et al., "Robotic Endoscope Control Via Autonomous Instrument Tracking," Frontiers in Robotics and AI, vol. 9, pp. 1-22 (Apr. 2022).

* cited by examiner

ROBOTIC BRONCHOSCOPY NAVIGATION METHOD AND SYSTEM

CROSS-REFERENCE TO RELATED APPLICATIONS

This non-provisional application claims priority under 35 U.S.C. § 119(a) on Patent Application No(s). 111133314 filed in Republic of China (ROC) on Sep. 2, 2022, the entire contents of which are hereby incorporated by reference.

BACKGROUND

1. Technical Field

This disclosure relates to a robotic bronchoscopy navigation method and system.

2. Related Art

In the existing robotic bronchoscopy navigation technology, the operator or system controller of the bronchoscopy must know various information before surgery, such as the position of the end of the bronchus, the shape of the bronchus, etc. to determine how to manipulate the bronchoscopy (such as distance, direction, and orientation of moving the bronchoscopy). However, the method of obtaining the information above mentioned depends on the preoperative medical images, and the medical images obtained before the operation are still not identical with the actual images during the operation. For example, the difference may be resulted from breathing, posture of the patient. Therefore, the operator or system controller is still unable to obtain the accurate position to be operated or examined during the operation.

SUMMARY

According to one or more embodiment of this disclosure, a robotic bronchoscopy navigation method, performed by a processing control device, includes: obtaining a navigation image, and performing a navigation procedure according to the navigation image, the navigation procedure including: determining whether the navigation image has a node; if the navigation image does not have the node, controlling a bending part of a robotic bronchoscopy to move toward an image center of the navigation image; if the navigation image has the node, calculating a distance between the bronchoscopy tip and the node; controlling the bending part to move according to a default branch when the distance is smaller than a threshold of distance; and determining whether the default branch is a destination branch where a destination is located; if the default branch is not the destination branch, obtaining another navigation image, and performing the navigation procedure on the another navigation image; and if the default branch is the destination branch, outputting a notification.

According to one or more embodiment of this disclosure, a robotic bronchoscopy navigation system includes: a robotic arm and a processing control device. The robotic arm is configured to control a robotic bronchoscopy. The processing control device is connected to the robotic arm to control the robotic bronchoscopy through the robotic arm, wherein the processing control device is configured to: obtaining a navigation image, and performing a navigation procedure according to the navigation image, the navigation procedure including: determining whether the navigation image has a node; if the navigation image does not have the node, controlling a bending part of the robotic bronchoscopy to move toward an image center of the navigation image; if the navigation image has the node, calculating a distance between the bronchoscopy tip and the node; controlling the bending part to move according to a default branch when the distance is smaller than a threshold of distance; and determining whether the default branch is a destination branch where a destination is located; if the default branch is not the destination branch, obtaining another navigation image, and performing the navigation procedure on the another navigation image; and if the default branch is the destination branch, outputting a notification.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present invention. The following embodiments further illustrate various aspects of the present invention, but are not meant to limit the scope of the present invention.

Figure 1:
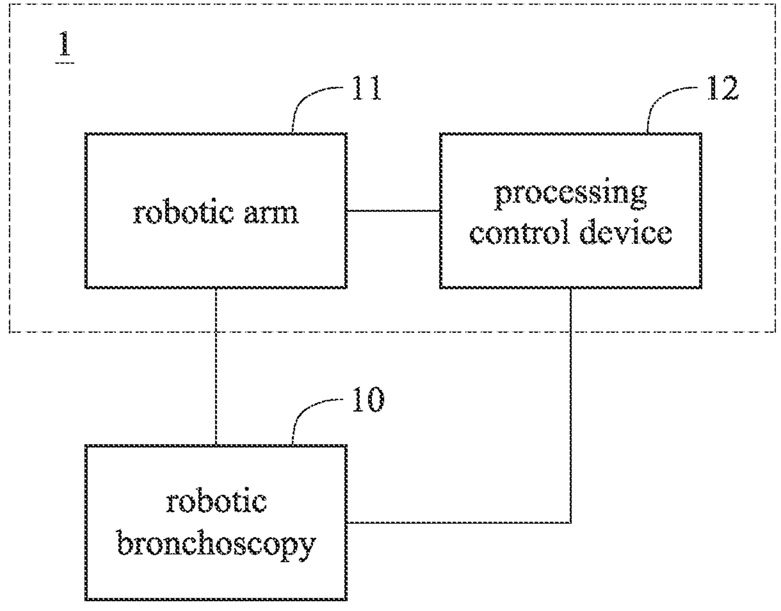
FIG. 1 is a block diagram illustrating a robotic bronchoscopy navigation system according to an embodiment of the present disclosure.

Please refer to FIG. 1, wherein FIG. 1 is a block diagram illustrating a robotic bronchoscopy navigation system according to an embodiment of the present disclosure. The robotic bronchoscopy navigation system 1 includes a robotic arm 11 and a processing control device 12. The processing control device 12 is electrically connected to or in communication connection with a robotic bronchoscopy 10 and the robotic arm 11. For example, the processing control device 12 may be connected to the robotic arm 11 through the bus system of Ethernet for control automation technology (EtherCAT). The robotic arm 11 is configured to grip the robotic bronchoscopy 10, and the processing control device 12 is configured to control the movement of the bronchoscopy 10 through the robotic arm 11, thereby obtaining images of bronchus captured by the robotic bronchoscopy 10. Specifically, the robotic bronchoscopy 10 may be controlled by a DC servo, for the robotic arm 11 to manipulate the movement of the robotic bronchoscopy 10. In addition, a bending part of the robotic bronchoscopy 10 may be provided with a USB LED strip light and a camera, wherein the bending part is at a tip of the robotic bronchoscopy 10, and the LED strip light is used to illuminate the interior of the bronchus, and the camera is used to obtain images inside the bronchus during operation process. Further, images obtained by the camera may be fed back to the processing control device 12 in real time.

The robotic arm 11 may be a triaxial robotic arm, a tetraxon robotic arm or a six-axis robotic arm etc., the present disclosure is not limited thereto. The processing control device 12 may include a central processing unit, a programmable logic array (PLA) or an application specific integrated circuit (ASIC) etc., and the processing control device 12 and a controller (for example, a motion controller) may be integrated into one device, the present disclosure is not limited thereto.

Figure 2:
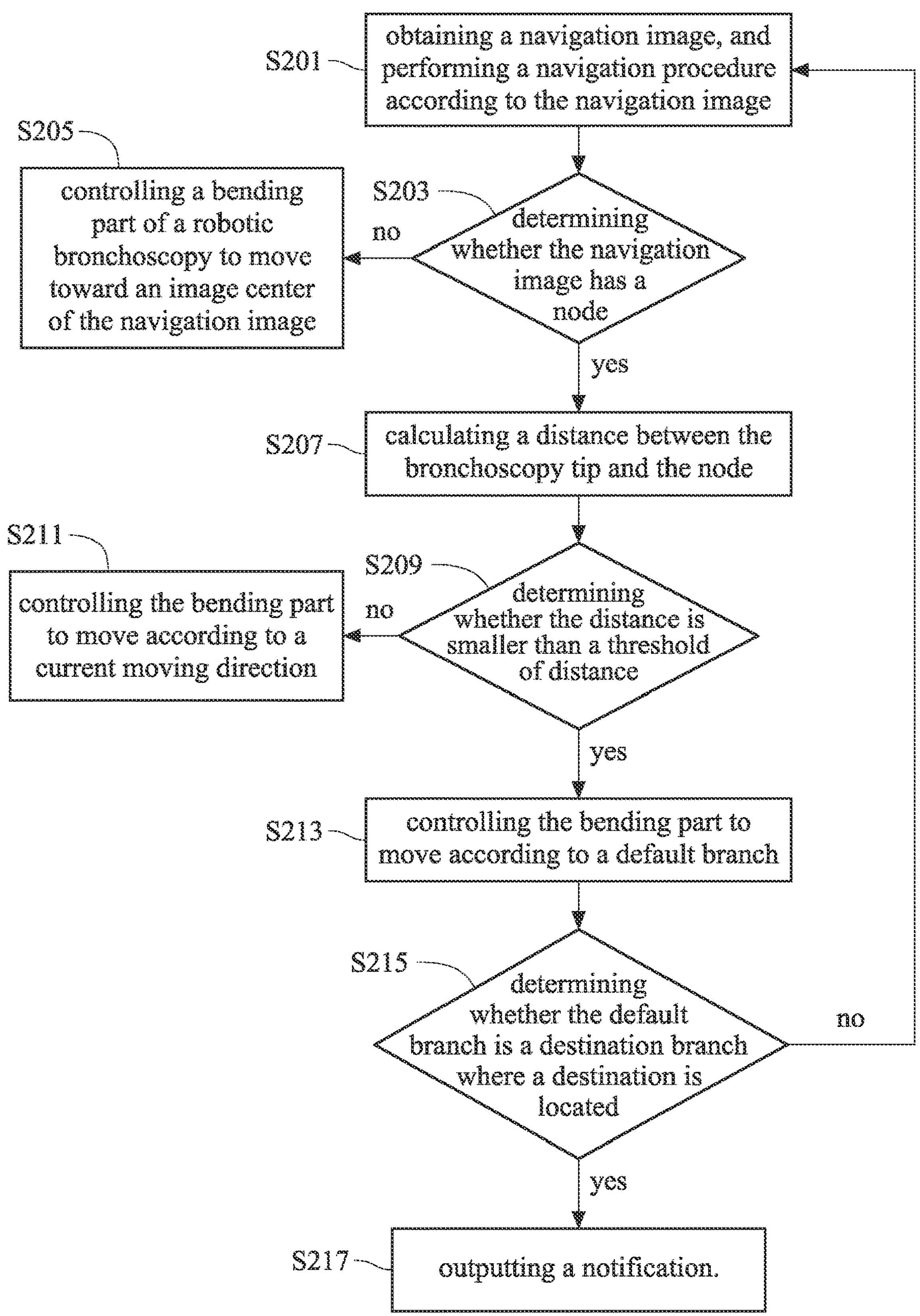
FIG. 2 is a flowchart illustrating a robotic bronchoscopy navigation method according to an embodiment of the present disclosure.
Figures 3A, 3B:
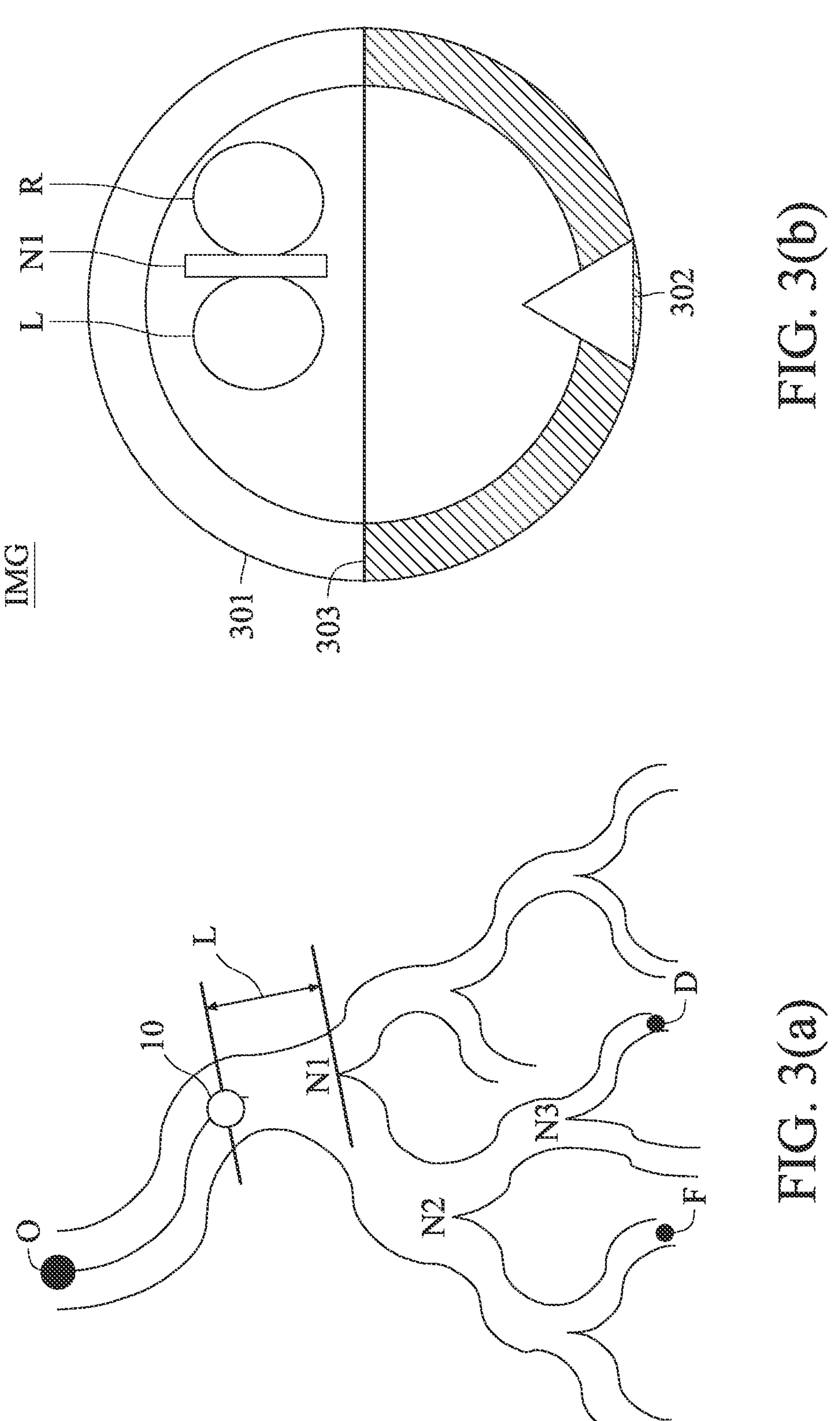
FIG. 3(*a*) of complete bronchi, FIG. 3(*b*) is a schematic diagram of a navigation image.

Please refer to FIG. 1, FIG. 2, FIG. 3(*a*) and FIG. 3(*b*), wherein FIG. 2 is a flowchart illustrating a robotic bronchoscopy navigation method according to an embodiment of the present disclosure, FIG. 3(*a*) is a schematic diagram of complete bronchi, and FIG. 3(*b*) is a schematic diagram of a navigation image. As shown in FIG. 2, the robotic bronchoscopy navigation method according to an embodiment of the present disclosure, performed by the processing control device 12, includes: step S201: obtaining a navigation image, and performing a navigation procedure according to the navigation image; step S203: determining whether the navigation image has a node; if the determination result of step S203 is "no", performing step S205: controlling a bending part of a robotic bronchoscopy to move toward an image center of the navigation image; if the determination result of step S203 is "yes", performing step S207: calculating a distance between the bronchoscopy tip and the node; step S209: determining whether the distance is smaller than a threshold of distance; if the determination result of step S209 is "no", performing step S211: controlling the bending part to move according to a current movement direction; if the determination result of step S209 is "yes", performing step S213: controlling the bending part to move according to a default branch; step S215: determining whether the default branch is a destination branch where a destination is located; if the determination result of step S215 is "no", performing step S201; and if the determination result of step S215 is "yes", performing step S217: outputting a notification.

It should be noted that, take FIG. 3(*a*) and FIG. 3(*b*) as an example, steps shown in FIG. 2 are for guiding the robotic bronchoscopy 10 to move from an origin O to a destination D shown in FIG. 3(*a*) during the surgery or examination, thereby avoiding the robotic bronchoscopy 10 being falsely operated and moved to a non-target area (for example, a false spot F shown in FIG. 3(*a*)). During navigation, images obtained by the camera of the robotic bronchoscopy 10 may be a navigation image IMG shown in FIG. 3(*b*). The navigation image IMG includes a horizontal level measurement image 301 and a horizontal level measurement index 302 shown in double concentric circles, and includes an image of the interior of the bronchus, wherein said image is presented inside the inner circle of the horizontal level measurement image 301. The details of the horizontal level measurement image 301 and the horizontal level measurement index 302 are described later.

In step S201, the processing control device 12 obtains the navigation image IMG from the robotic bronchoscopy 10. After obtaining the navigation image IMG, the processing control device 12 performs the navigation procedure according to the navigation image IMG, to determine next moving direction of the robotic bronchoscopy 10, wherein the navigation procedure includes steps S203, S205, S207 and S209.

In step S203, the processing control device 12 determines whether a bifurcation point (node) of the bronchus exists in the navigation image IMG. In short, the processing control device 12 determines whether the navigation image IMG presents two bronchi to determine whether the bifurcation point of the bronchus exists in the navigation image IMG. Take FIG. 3(*b*) as an example, in step S203, the processing control device 12 determines whether the navigation image IMG has a node N1 between a left bronchus L and a right bronchus R, or determine whether the navigation image IMG shows the left bronchus L and the right bronchus R at the same time.

If the processing control device 12 determines that the navigation image IMG does not have the node N1, the processing control device 12 performs step S205, to control the bending part of the robotic bronchoscopy 10 to move toward an image center of the navigation image IMG through the robotic arm 11, for centering the bending part of the robotic bronchoscopy 10 to the image center of the navigation image IMG. Preferably, when performing said centering, the processing control device 12 controls the bending part of the robotic bronchoscopy 10, through the robotic arm 11, to stay horizontally.

If the processing control device 12 determines that the navigation image IMG has the node N1, the processing control device 12 performs step S207 to calculate a distance L between the bending part of the robotic bronchoscopy 10 and the node N1. Also take FIG. 3(*a*) as an example, the location of the robotic bronchoscopy 10 in the bronchus and the location of the node N1 in the bronchus are as shown in FIG. 3(*a*). The processing control device 12 performing step S207 to calculate the distance L may be implemented with the following equation (1):

$$\frac{\text{focal length } d}{\text{sensor diameter } t} = \frac{\text{bronchus diameter } T}{distanceL} \quad \text{[equation (1)]}$$

wherein the sensor diameter t is the diameter of the bending part (the camera) of the robotic bronchoscopy 10; the focal length d is the focal length of the bending part (the camera) of the robotic bronchoscopy 10; and the bronchus diameter T is a sum of a diameter of the left bronchus L and a diameter of the right bronchus R.

In step S209, the processing control device 12 determines whether the distance L is smaller than the threshold of distance, to determine whether the bending part of the robotic bronchoscopy 10 is close enough to the node N1. The threshold of distance is, for example, 1.5 centimeters, but the present disclosure is not limited thereto.

If the processing control device 12 determines that the distance L is not smaller than the threshold of distance, then in step S211, the processing control device 12 controls, through the robotic arm 11, the bending part of the robotic bronchoscopy 10 to move according to the current movement direction. Take FIG. 3(*a*) as an example, the current movement direction is a direction from the origin O to the node N1; and in step S211, the processing control device 12 controls, through the robotic arm 11, the bending part of the robotic bronchoscopy 10 to move closer to the node N1.

If the processing control device 12 determines that the distance L is smaller than the threshold of distance, then in step S213, the processing control device 12 controls the bending part of the robotic bronchoscopy 10 to move according to a default branch, wherein the default branch is one of the preplanned navigation paths. The processing control device 12 may control the bending part of the robotic bronchoscopy 10 to move from the origin O to the destination D according to a number of default branches. Take FIG. 3(*a*) and FIG. 3(*b*) as an example, after the bending part of the robotic bronchoscopy 10 is close enough to the first node N1, if the default branch is a left-side branch, the processing control device 12 may control the bending part of the robotic bronchoscopy 10 to move toward the left bronchus L.

In step S215, the processing control device 12 determines whether the default branch is the destination branch that the destination O is located at, to determine whether the bending part of the robotic bronchoscopy 10 has arrived at the destination O. If the processing control device 12 determines that the default branch is not the destination branch that the destination O is located at, the processing control device 12 performs step S201 to obtain another navigation image, to perform the navigation procedure on said another navigation image. If the processing control device 12 determines that the default branch is the destination branch that the destination O is located at, the processing control device 12 may output the notification, wherein the notification is used to notify the user that the bending part of the robotic bronchoscopy 10 has arrived at the destination O. That is, the bending part has arrived at a to-be-operated or to-be-examined site in the bronchus. It should be noted that, the processing control device 12 may output the notification to a terminal device (for example, a computer, a mobile phone, or a tablet etc.) of the user. The processing control device 12 may also output the notification to a cloud server that is accessible to the user. The present disclosure is not limited thereto.

In addition, in a situation where the purpose of the processing control device 12 is to guide the bending part of the robotic bronchoscopy 10 to the destination O, in the example of FIG. 3(*a*), the processing control device 12 may first control the bending part of the robotic bronchoscopy 10 to move toward the first node N1 (depending on the current location of the bending part, it may also be a second node N2 or a third node N3) with a default distance.

Then, the processing control device 12 determines whether the distance L between the bending part of the robotic bronchoscopy 10 and the node N1 is smaller than the threshold of distance. If the distance L is not smaller than the threshold of distance, the processing control device 12 performs step S211; and if the distance L is smaller than the threshold of distance, the processing control device 12 performs step S213.

When the processing control device 12 controls the bending part of the robotic bronchoscopy 10 to move toward the first node N1 for the default distance, the processing control device 12 may calculate a vector of the first node N1 relative to the image center (for example, a center of the robotic bronchoscopy 10), and control the bending part of the robotic bronchoscopy 10 to move toward the first node N1 according to the vector, for the first node N1 to be aligned with the image center. In other words, take the location of the first node N1 shown in FIG. 3(*b*) as an example, the processing control device 12 may control, through the robotic arm 11, the bending part of the robotic bronchoscopy 10 to move toward the wall of the right bronchus (toward top-right of the navigation image IMG).

Figure 4:
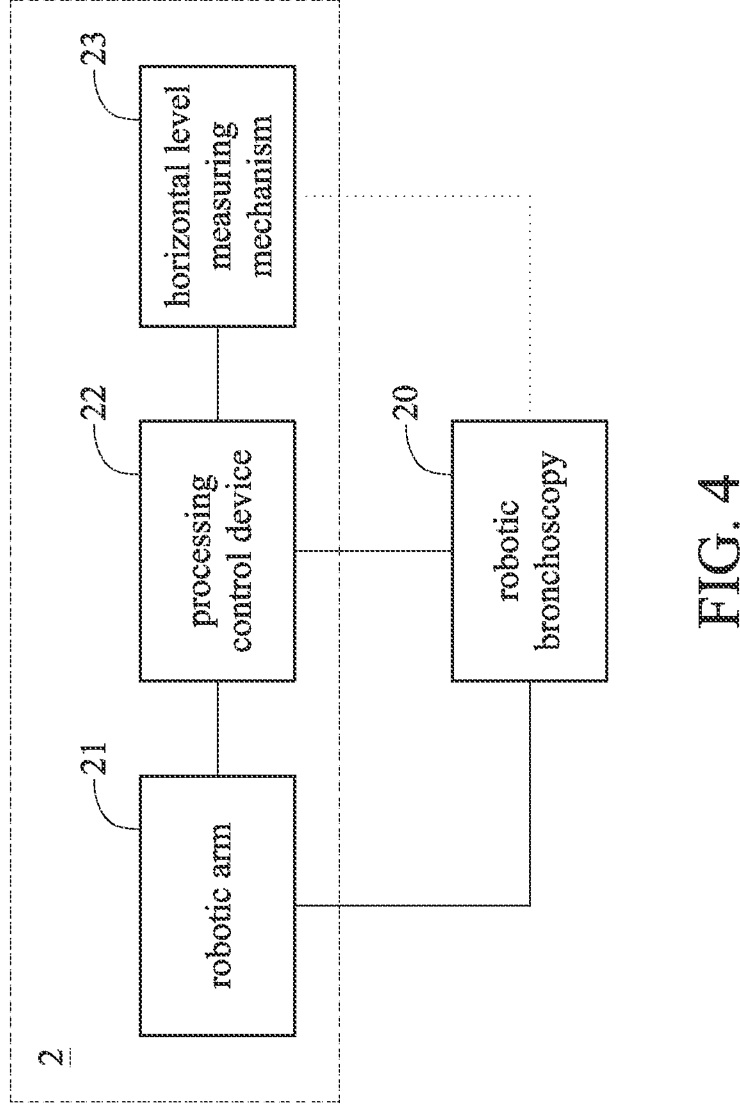
FIG. 4 is a block diagram illustrating a robotic bronchoscopy navigation system according to another embodiment of the present disclosure.

Please refer to FIG. 3(*b*) and FIG. 4, wherein FIG. 4 is a block diagram illustrating a robotic bronchoscopy navigation system according to another embodiment of the present disclosure. The robotic bronchoscopy navigation system 2 shown in FIG. 4 includes a robotic arm 21, a processing control device 22 and a horizontal level measuring mechanism 23, wherein the robotic arm 21 shown in FIG. 4 may be the same as the robotic arm 11 shown in FIG. 1, and the processing control device 22 shown in FIG. 4 may be the same as the processing control device 12 shown in FIG. 1. Therefore, the repeated descriptions thereof are omitted.

The difference between the embodiment of FIG. 4 and embodiment of FIG. 1 is that, the robotic bronchoscopy navigation system 2 further includes the horizontal level measuring mechanism 23. The horizontal level measuring mechanism 23 is disposed on the robotic bronchoscopy 20, and is preferably disposed on the bending part of the robotic bronchoscopy 20. The horizontal level measuring mechanism 23, for example, presents the liquid level or the position of the bubble in the closed pipeline around the lens (for example, the lens of the robotic bronchoscopy 20) on the image with its subjection to gravity. When the robotic bronchoscopy 20 is taking images of the bronchus, the robotic bronchoscopy 20 also obtains the level status from the horizontal level measuring mechanism 23, and presents the horizontal level status on an image (for example, the navigation image) in the form of a picture, thereby obtaining the horizontal level measurement image 301, the horizontal level measurement index 302 and a horizontal level surface 303.

Specifically, take a horizontal level gauge as example, which shows horizontal level status with the horizontal level surface, the navigation image IMG includes the horizontal level measurement image 301, and the horizontal level measurement image 301 includes the horizontal level measurement index 302 shown in a triangle form in FIG. 3(*b*) and the horizontal level surface 303. In the horizontal level measurement image 301, an upper half of the horizontal level surface 303 corresponds to the abdomen of the patient, and a lower half of the horizontal level surface 303 corresponds to the back of the patient. The horizontal level measurement index 302 is fixed on the horizontal level measuring mechanism 23. Therefore, the horizontal level measurement index 302 may move along with the movement of the robotic bronchoscopy 10 in the bronchus. For example, horizontal level measurement index 302 may rotate along with the rotation of the robotic bronchoscopy 10, and the horizontal level measurement index 302 and the robotic bronchoscopy 10 have the same rotation angle.

The horizontal level surface 303 is at all times perpendicular to the direction of gravity. Therefore, when the processing control device 22 obtains the navigation image IMG, the processing control device 22 may perform image recognition on the navigation image IMG to identify the horizontal level measurement index 302 and the horizontal level surface 303 in the navigation image IMG. Then, the processing control device 22 may determine a relative position between the horizontal level measurement index 302 and the horizontal level surface 303, thereby determining whether the posture or orientation of the robotic bronchoscopy 10 in the bronchus should be adjusted. For example, the processing control device 22 may determine whether to rotate the robotic bronchoscopy 10 for a straight line connecting the center of the horizontal level surface 303 with the horizontal level measurement index 302 to be in parallel with the direction of gravity.

Moreover, for example, the processing control device 22 may pre-store the pattern corresponding to the horizontal level measurement index 302, a first color representing liquid part and a second color representing non-liquid part, wherein the pattern in the present example is the triangle pattern shown in FIG. 3(*b*). When the processing control device 22 obtains the navigation image IMG, the processing control device 22 identifies the horizontal level measurement index 302 in the navigation image IMG by object detection, and determines a boundary between the first color and the second color as the horizontal level surface 303. Then, the processing control device 22 obtains the relative position between the horizontal level measurement index 302 and the horizontal level surface 303.

The example shown in FIG. 3(*b*) is the horizontal level measurement index 302 indicating a horizontal state, wherein the horizontal state means the relative position between the horizontal level measurement index 302 and the horizontal level surface 303 being: the horizontal level measurement index 302 locates at a region of the first color and a straight connection line between the horizontal level measurement index 302 and the center of the horizontal level surface 303 is parallel to the gravity direction. When the horizontal level measurement index 302 indicates the horizontal state, the processing control device 22 may not adjust the posture of the robotic bronchoscopy 10 in the bronchus.

If the horizontal level measurement index 302 locates at the right semicircle of the horizontal level measurement image 301 and causes the relative position between the horizontal level measurement index 302 and the horizontal level surface 303 to indicate that the straight connection line between the horizontal level measurement index 302 and the center of the horizontal level surface 303 is not parallel to the gravity direction, the robotic bronchoscopy 20 is not in the horizontal state. Therefore, before determining whether the navigation image IMG has the node, the processing control device 22 may control, through the robotic arm 21, the bending part of the robotic bronchoscopy 20 to rotate clockwise.

If the horizontal level measurement index 302 locates at the left semicircle of the horizontal level measurement image 301 and causes the relative position between the horizontal level measurement index 302 and the horizontal level surface 303 being that the straight connection line between the horizontal level measurement index 302 and the center of the horizontal level surface 303 to not be in parallel to the gravity direction, the robotic bronchoscopy 20 is not in the horizontal state. Therefore, before determining whether the navigation image IMG has the node, the processing control device 22 may control, through the robotic arm 21, the bending part of the robotic bronchoscopy 20 to rotate counterclockwise.

In short, the processing control device 22 may control the rotation direction of the bending part of the robotic bronchoscopy 20 according to the horizontal level measurement index 302 for the horizontal level measurement index 302 to indicate the horizontal state. Accordingly, the relative position between the node and the bronchus in the navigation image IMG may be accurately determined.

Figure 5:
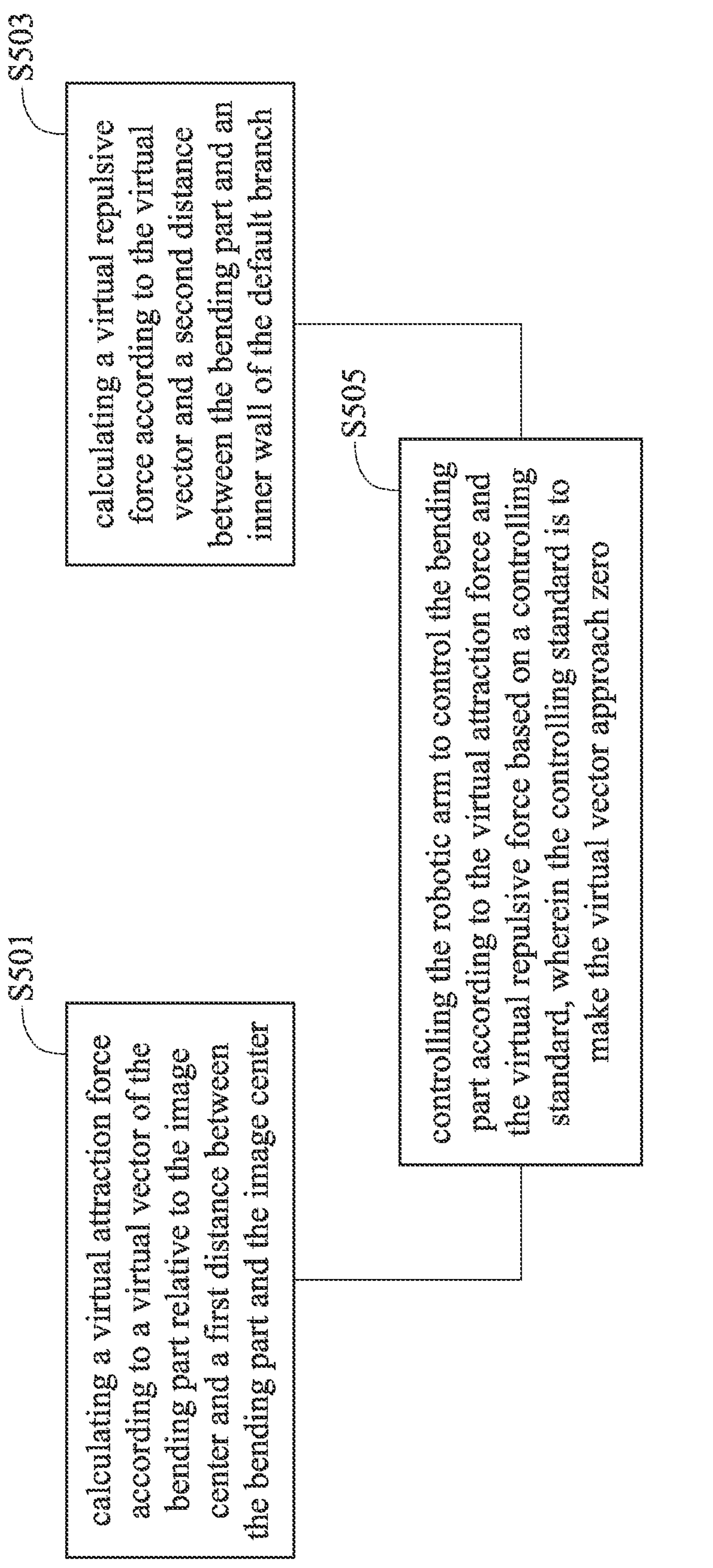
FIG. 5 is a flowchart illustrating a method of controlling a bending part of a robotic bronchoscopy to move forward.
Figure 6:
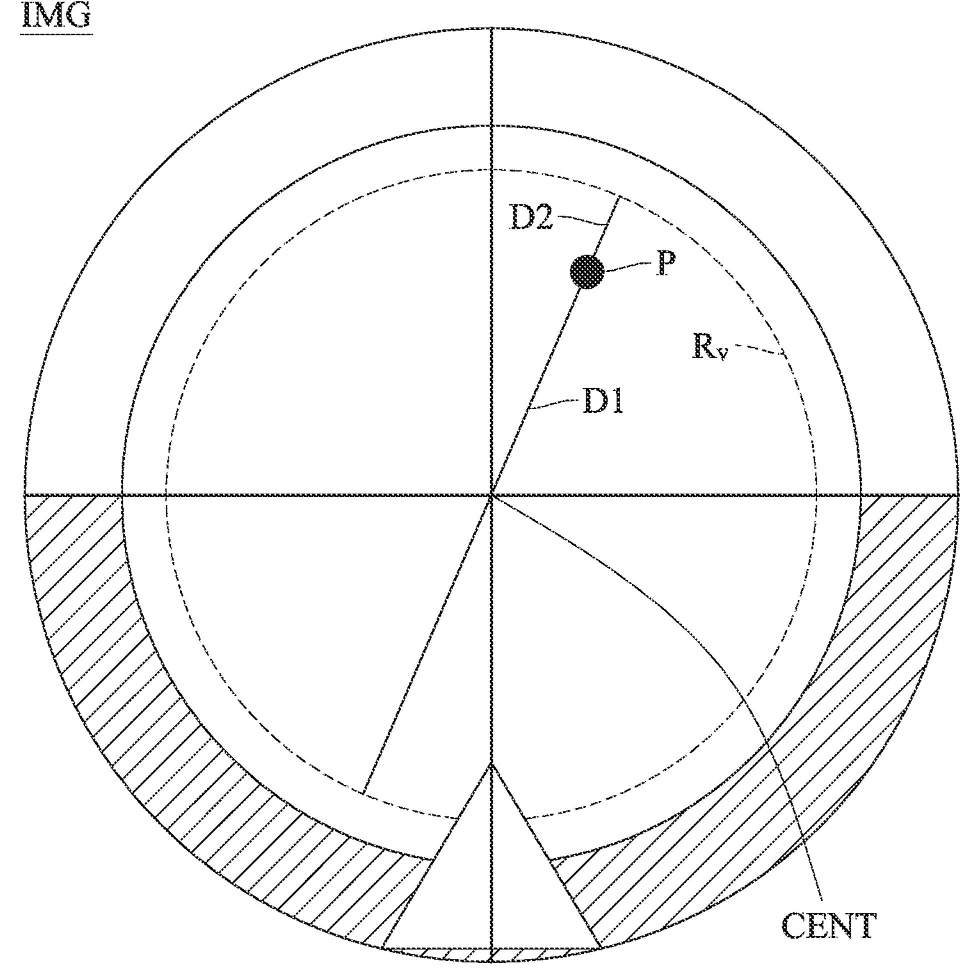
FIG. 6 is a schematic diagram illustrating method of calculating a virtual repulsive force and a virtual attraction force.

Please refer to FIG. 1, FIG. 5 and FIG. 6, wherein FIG. 5 is a flowchart illustrating a method of controlling a bending part of a robotic bronchoscopy to move forward, step S213 shown in FIG. 2 may include steps shown in FIG. 5, and FIG. 6 is a schematic diagram illustrating method of calculating a virtual repulsive force and a virtual attraction force. As shown in FIG. 5, step S213 of FIG. 2 may include: step S501: calculating a virtual attraction force according to a virtual vector of the bending part relative to the image center and a first distance between the bending part and the image center; step S503: calculating a virtual repulsive force according to the virtual vector and a second distance between the bending part and an inner wall of the default branch; and step S505: controlling the robotic arm to control the bending part according to the virtual attraction force and the virtual repulsive force based on a controlling standard, wherein the controlling standard is to make the virtual vector approach zero. It should be noted that, step S501 and step S503 may be performed in parallel, step S501 may also be performed before or after step S503, the present disclosure is not limited thereto.

FIG. 6 shows an example of the navigation image IMG presenting the default branch, wherein the navigation image IMG includes a virtual desired location P (represented as a vector originated from CENT) of the bending part of the robotic bronchoscopy 10, the image center CENT of the navigation image IMG, a first distance D1 between the virtual desired location P of the bending part and the image center CENT, and a second distance D2 between the virtual desired location P of the bending part and an inner wall of the default branch. The virtual desired location P, the image center CENT, the first distance D1 and the second distance D2 shown in FIG. 6 are illustrated for the convenience of description, and during actual practice, the navigation image IMG may not show the virtual desired location P, the image center CENT, the first distance D1 and the second distance D2.

In step S501, the processing control device 12 may calculate the virtual attraction force F1 with the following equation (2) according to the first distance D1 and the virtual vector P originated from the image center CENT:

$$F1 = \frac{M_1\ddot{P} + B_1\dot{P} + K_1P}{D_1^2} \quad \text{[equation (2)]}$$

wherein in equation (2), $M_1$, $B_1$ and $K_1$ are force generation coefficients; P is the virtual vector; $\dot{P}$ is the speed obtained by performing first order differentiation on the virtual vector; $\ddot{P}$ is the acceleration obtained by performing second order differentiation on the virtual vector.

In step S503, the processing control device 12 may calculate the virtual repulsive force F2 with the following equation (3) according to the second distance D2 and the virtual vector P originated from the image center CENT:

$$F2 = \frac{M_2\ddot{P} + B_2\dot{P} + K_2P}{D_2^2} \quad \text{[equation (3)]}$$

wherein in equation (3), $M_2$, $B_2$ and $K_2$ are force generation coefficients; P is the virtual vector; is the speed obtained by performing first order differentiation on the virtual vector; $\ddot{P}$ is the acceleration obtained by performing second order differentiation on the virtual vector.

The force generation coefficients in equation (2) may be the same as or different from the force generation coefficients in equation (3), respectively. The force generation coefficients of equation (2) and equation (3) may be set according to an application scenario. For example, in a scenario where the virtual attraction force and the virtual repulsive force are required to be more sensitive to the moving speed and acceleration of the robotic bronchoscopy 10, the values of the force generation coefficients $M_1$, $B_1$, $M_2$ and $B_2$ may be increased. In a scenario where the virtual attraction force and the virtual repulsive force are required to be more sensitive to the virtual vector of the robotic bronchoscopy 10, the values of the force generation coefficients $K_1$ and $K_2$ may be increased, or the values of the force generation coefficients $M_1$, $B_1$, $M_2$ and $B_2$ may be set to zero.

In step S505, the processing control device 12 controls the robotic arm 11 to control the bending part of the robotic bronchoscopy 10 to move, for the location P to be located at the image center CENT, and the virtual vector is zero.

Take FIG. 6 as an example, if the location P locates at the image center CENT, the bending part of the robotic bronchoscopy 10 is subjected to the strongest virtual attraction force; and if the location P reaches to the wall, the bending part of the robotic bronchoscopy 10 is subjected to the strongest virtual repulsive force. Specifically, if the first distance D1 is greater than the second distance D2 for the virtual repulsive force to be greater than the virtual attraction force, the bending part of the robotic bronchoscopy 10 may be seen as being pushed to the image center CENT by the virtual repulsive force. On the contrary, if the first distance D1 is smaller than the second distance D2 for the virtual repulsive force to be smaller than the virtual attraction force, the bending part of the robotic bronchoscopy 10 may be seen as being pulled to the image center CENT by the virtual attraction force; and if the first distance D1 equals to the second distance D2, it may be seen as the virtual repulsive force equals to the virtual attraction force, the bending part of the robotic bronchoscopy 10 locates at the image center CENT, and the virtual vector equals to zero. In short, the virtual attraction force may be regarded as the accelerator for accelerating the bending part of the robotic bronchoscopy 10 to approach the image center CENT, and the virtual repulsive force may be regarded as a brake to prevent the bending part of the robotic bronchoscopy 10 from contacting the wall of the bronchus.

In addition, the virtual repulsive force may be calculated based on a virtual inner wall $R_v$ of FIG. 6. Specifically, the second distance D2 may be the distance between the location P and the virtual inner wall $R_v$, and a radius of the virtual inner wall $R_v$ is smaller than the actual radius of the default branch. Accordingly, when the bending part of the robotic bronchoscopy 10 approaches the virtual inner wall $R_v$, since the virtual repulsive force is strong enough and the bending part of the robotic bronchoscopy 10 is seen as being pushed away from the virtual inner wall $R_v$, the bending part of the robotic bronchoscopy 10 may be prevented from contacting the bronchus the wall, thereby lowering the risk of the bronchus being injured because of direct contact with the robotic bronchoscopy 10.

Moreover, the processing control device 12 may control the robotic arm 11 to manipulate the robotic bronchoscopy 10 with the following equation (4) to equation (8) according to the virtual attraction force and the virtual repulsive force. "F" in equation (4) to equation (8) may be the virtual repulsive force or the virtual attraction force; coefficient M may be $$\frac{M_1}{D_1^2} \text{ or } \frac{M_2}{D_2^2};$$

coefficient B may be $$\frac{B_1}{D_1^2} \text{ or } \frac{B_2}{D_2^2};$$

coefficient K may be $$\frac{K_1}{D_1^2} \text{ or } \frac{K_2}{D_2^2}.$$

Equation (4) is the kinetic equation for controlling the robotic bronchoscopy 10; equation (5) is derived based on the impedance control law, and the torque required to drive and manipulate the bending part of the robotic bronchoscopy 10. The processing control device 12 may substitute equation (5) in equation (4), and substitute joint variables q of the robotic bronchoscopy 10 in equation (4), to obtain equation (6) and equation (7). Then, equation (8) is obtained through equation (7), wherein the form of equation (8) and the form of equation (2) or equation (3) are equivalent. In short, the processing control device 12 may substitute the virtual attraction force and the virtual repulsive force in equation (4) to equation (8) to obtain the torque, and control the operation of servo motors to manipulate the bending section of the robotic bronchoscopy 10.

$$H(q)\dot{q}+V(q,\ddot{q})+G(q)\doteq\tau+J^T(q)F \quad \text{[equation (4)]}$$

$$\tau_{act}=HJ^{-1}M^{-1}K(-P)HJ^{-1}M^{-1}B(-P)+HJ^{-1}M^{-1}F-J^TF-HJ^{-1}\dot{J}\dot{q}+V+G \quad \text{[equation (5)]}$$

$$H\ddot{q}+HJ^{-1}\dot{J}\dot{q}+HJ^{-1}M^{-1}K(-P)+HJ^{-1}M^{-1}B(-\dot{P})=HJ^{-1}M^{-1}F \quad \text{[equation (6)]}$$

$$HJ^{-1\ddot{P}}+HJ^{-1}M^{-1}K(P)+HJ^{-1}M^{-1}B(\dot{P})=HJ^{-1}M^{-1}F \quad \text{[equation (7)]}$$

$$\ddot{P}+M^{-1}KP+M^{-1}B\ddot{P}=M^{-1}F \quad \text{[equation (8)]}$$

Therefore, according to equation (4) to equation (8), the processing control device 12 may control the robotic arm 11 to manipulate the robotic bronchoscopy 10, wherein relationships between the location P, the virtual attraction force and the virtual repulsive force are regulated by equation (2) and equation (3).

Figure 7:
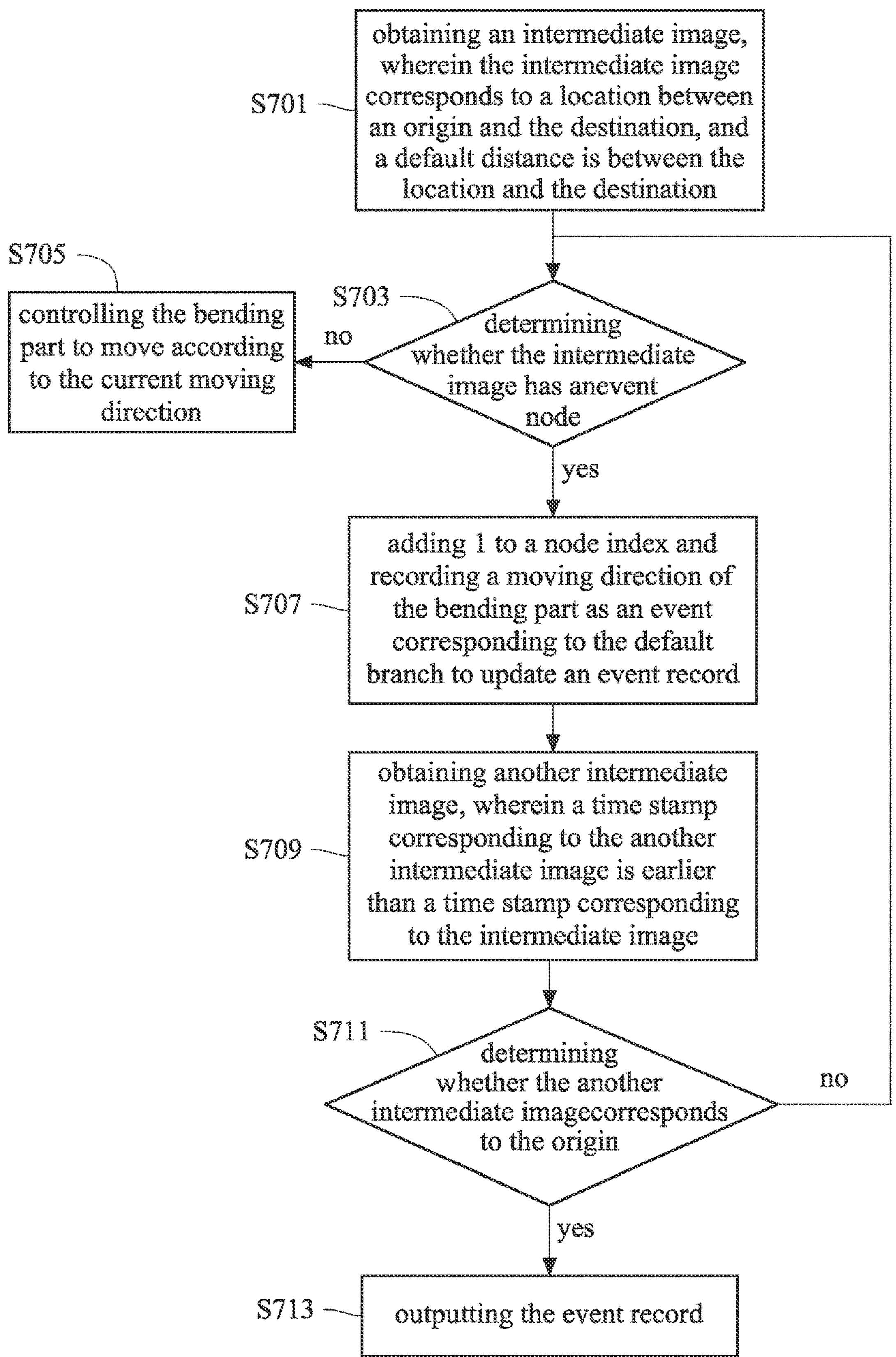
FIG. 7 is a flowchart illustrating a path planning procedure according to an embodiment of the present disclosure.
Figure 8:
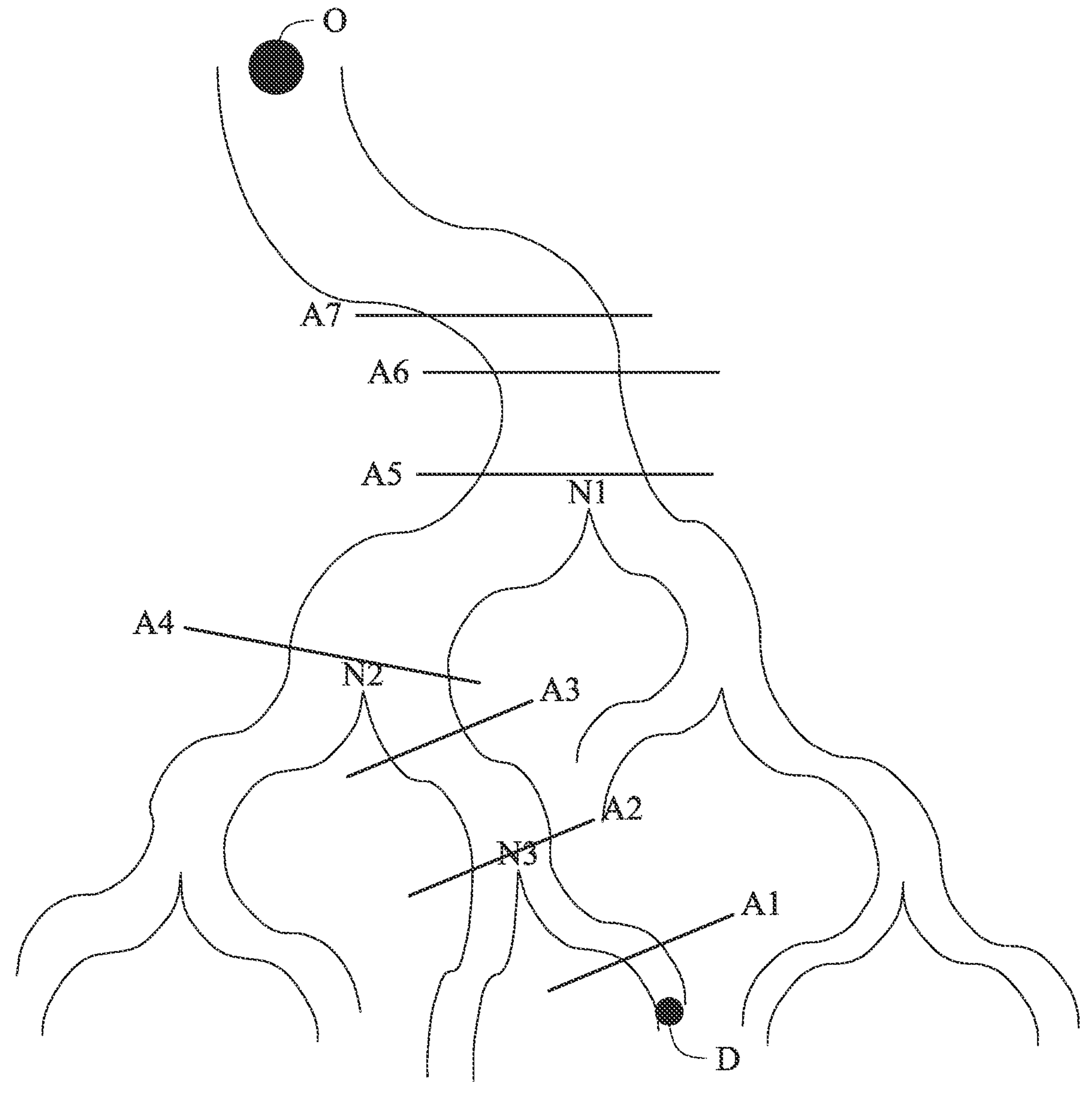
FIG. 8 is a schematic diagram illustrating the path planning procedure.

Please refer to FIG. 1, FIG. 7 and FIG. 8, wherein FIG. 7 is a flowchart illustrating a path planning procedure according to an embodiment of the present disclosure, and FIG. 8 is a schematic diagram illustrating the path planning procedure. The path planning procedure shown in FIG. 7 is used to plan the default branch described above, and is preferably performed sequentially from the first the cross section A1 to the origin O shown in FIG. 8. As shown in FIG. 7, the path planning procedure, performed by the processing control device 12, includes: step S701: obtaining an intermediate image, wherein the intermediate image corresponds to a location between an origin and the destination, and a default distance is between the location and the destination; step S703: determining whether the intermediate image has an event node; if the determination result of step S703 is "no", performing step S705: controlling the bending part to move according to the current movement direction; if the determination result of step S703 is "yes", performing step S707: adding 1 to a node index and recording a moving direction of the bending part as an event corresponding to the default branch to update an event record; step S709: obtaining another intermediate image, wherein a time stamp corresponding to the another intermediate image is earlier than a time stamp corresponding to the intermediate image; step S711: determining whether the another intermediate image corresponds to the origin; if the determination result of step S711 is "no", performing step S703: and if the determination result of step S711 is "yes", performing step S713: outputting the event record.

In step S701, the processing control device 12 obtains the intermediate image (referred to as "the first intermediate image" herein) that is near the destination D. That is, the first intermediate image is obtained by the robotic bronchoscopy 10, and is the image inside the bronchus and near the destination D. Further, the timing of the robotic bronchoscopy 10 obtaining the intermediate image is prior to performing the navigation procedure. Said "near the destination D" indicates that the distance between the destination D and the location corresponding to the first intermediate image in the bronchus is not greater than the default distance, wherein the default distance is, for example, 3 centimeters, but the present disclosure is not limited thereto. Then, the processing control device 12 performs a reverse acquisition procedure on the first intermediate image, wherein the reverse acquisition procedure includes steps S703, S705, S707, S709 and S711 shown in FIG. 7.

In step S703, the processing control device 12 determines whether the first intermediate image has the event node. The method of the processing control device 12 determining whether the first intermediate image has the event node may be the same as step S203 of FIG. 2, and detail description of step S703 is not repeated herein.

If the processing control device 12 determines that the first intermediate image does not have the event node, then in step S705, the processing control device 12 may control the bending part of the robotic bronchoscopy to move according to the current movement direction. Take FIG. 8 as an example, the processing control device 12 controls the bending part to move from the destination D to the cross section A1 site, and obtains the first intermediate image at the cross section A1 site. The current movement direction is a direction from the destination D to the cross section A1 site. At this time, the first intermediate image does not have the event node. Therefore, the processing control device 12 again controls, through the robotic arm 11, the bending part of the robotic bronchoscopy 10 to move along the bronchus according to the current movement direction.

If the processing control device 12 determines that the first intermediate image has the event node, then in step S707, the processing control device 12 may add 1 to the node index and record the moving direction of the bending part of the robotic bronchoscopy 10 as the event corresponding to the default branch to update the event record. An initial value of the node index may be 0. In other words, assuming the first intermediate image is the image at the cross section A2 site, and at this time, the first intermediate image has the event node (i.e. bifurcation point of the bronchus). Then, the processing control device 12 records an event corresponding to one default branch in the form of "node index i+moving direction". Moreover, the event corresponding to the cross section A2 may be "$TE_1=TN_1+R$", which means that when performing navigation according to the first event $TE_1$, a node $TN_1$ will be encountered during navigation, and when encountering this node $TN_1$, the robotic bronchoscopy should move toward the right (R side) bronchus of the third node N3. That is, "R" indicates the default branch of this event is the right bronchus of the third node N3, meaning the bronchus between the third node N3 and the destination D.

In step S709, the processing control device 12 obtains another intermediate image (referred to as "the second intermediate image" hereinafter), wherein a time stamp corresponding to the second intermediate image is earlier than the time stamp corresponding to the first intermediate image. Take FIG. 8 as an example, the second intermediate image is an image corresponding to the cross section A3. Further, since the sequence of image acquisition starts from the origin O to the destination D during the operation of obtaining a complete medical image of the bronchus as shown in FIG. 8, the time stamp of the second intermediate image corresponding to the cross section A3 is earlier than the time stamp of the first intermediate image corresponding to the cross section A2.

In step S711, the processing control device 12 determines whether the second intermediate image corresponds to the origin O to determine whether all default branches have been recorded. If the processing control device 12 determines that the second intermediate image does not correspond to the origin O, the processing control device 12 may perform step S703 again with the second intermediate image, to perform the reverse acquisition procedure on the second intermediate image. If the processing control device 12 determines that the second intermediate image corresponds to the origin O, the processing control device 12 may output the event record to the user end.

If the path planning procedure is performed on the bronchus shown in FIG. 8, the events recorded by the processing control device 12 correspond to the event nodes at the cross sections A2, A4 and A5. In other words, the event record includes event "$TE_1=TN_1+L$" at the cross section A2 site, event "$TE_2=TN_2+L$" at the cross section A4 site, and event "$TE_3=TN_3+R$" at the cross section A5 site; wherein "L" represents the left side.

Therefore, when performing navigation according to embodiments of the robotic bronchoscopy navigation method during surgery or examination, after the bending part of the robotic bronchoscopy 10 passes the origin O, the processing control device 12 determines to control the robotic bronchoscopy 10 to enter the right default branch (the bronchus between the first node N1 and the second node N2) when the first node ($TN_3$) is identified; control the robotic bronchoscopy 10 to enter the left default branch (the bronchus between the second node N2 and the third node N3) when the second node ($TN_2$) is identified; and control the robotic bronchoscopy 10 to enter the left default branch (the bronchus between the second node N2 and the destination D) when the third node ($TN_1$) is identified. Then, with step S215 of FIG. 2, the processing control device 12 determines the default branch that the bending part of the robotic bronchoscopy 10 currently locates at is the destination branch that the destination D locates at.

Figure 9:
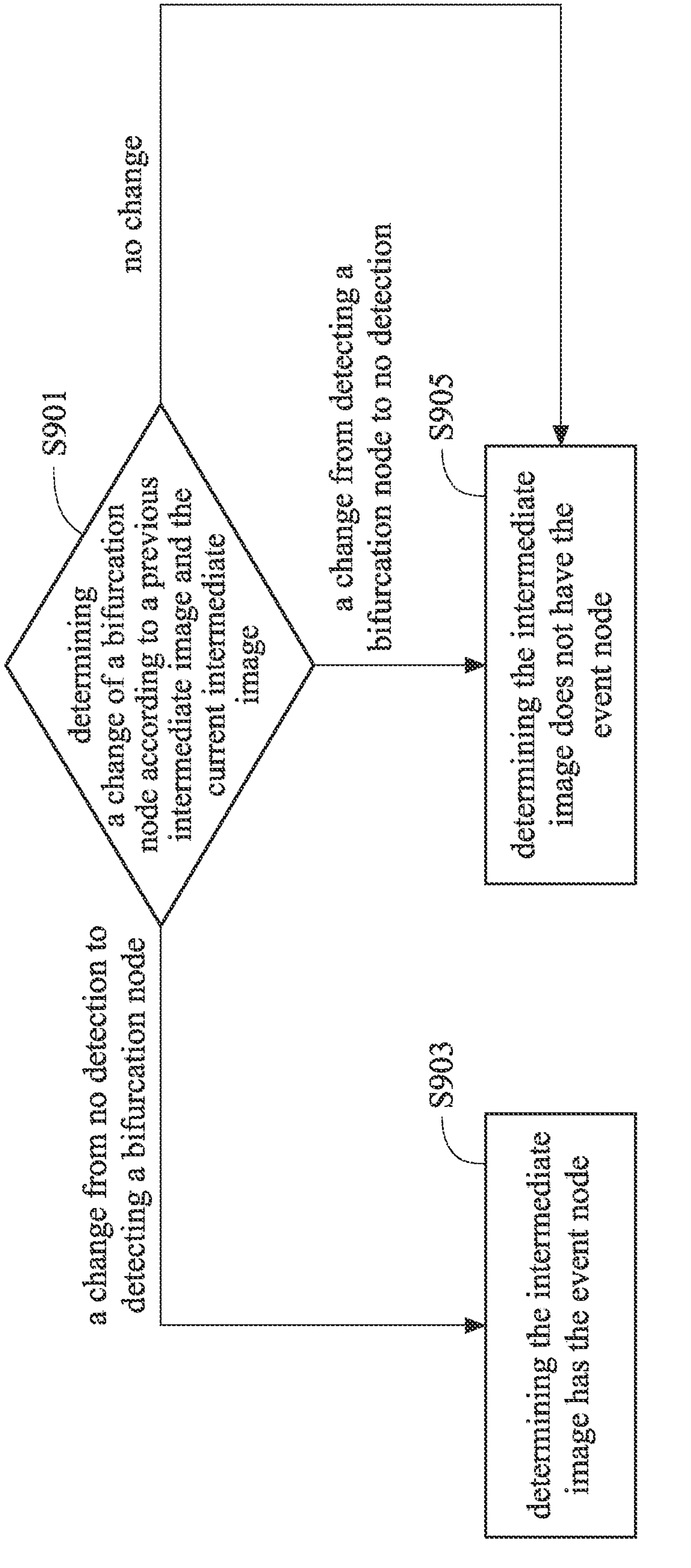
FIG. 9 illustrates a detail flowchart of step S703 of FIG. 7.

Please refer to FIG. 1, FIG. 8 and FIG. 9, wherein FIG. 9 illustrates a detail flowchart of step S703 of FIG. 7. As shown in FIG. 9, step S703 of FIG. 7 may include: step S901: determining a change of a bifurcation node according to a previous intermediate image and the current intermediate image; if the determination result of step S901 is "a change from no detection to detecting a bifurcation node", performing step S903: determining the intermediate image has the event node; if the determination result of step S901 is "a change from detecting a bifurcation node to no detection", performing step S905: determining the intermediate image does not have the event node; and if the determination result of step S901 is "no change", performing step S905. In short, the processing control device 12 may determine whether the event node is detected according to the changes from one frame of intermediate image to another frame of intermediate image.

Take the intermediate images corresponding to the cross sections A1 and A2 shown in FIG. 8 as an example, the processing control device 12 determines that a bifurcation node is not detected in the previous intermediate image at the cross section A1 site, and a bifurcation node (N3) is detected in the current intermediate image at the cross section A2 site. Therefore, the processing control device 12 uses the bifurcation node detected in the current intermediate image as the event node (step S903).

Then, the robotic bronchoscopy 10 moves from the cross section A2 site to the cross section A3 site, wherein the image at the cross section A2 site is the previous intermediate image, and the image at the cross section A3 site is the current intermediate image. The processing control device 12 determines that a bifurcation node is not detected in the current intermediate image at the cross section A3 site, and the processing control device 12 determines that the current intermediate image does not have the event node. Therefore, the processing control device 12 determines that the change of the bifurcation node is a change from having detection at the cross section A2 site to no detection of a bifurcation node at the cross section A3 site, and does not update the event record according to the current intermediate image at the cross section A3 (step S905).

Take the intermediate images corresponding to the cross sections A6 and A7 shown in FIG. 8 as an example, the processing control device 12 determines that a bifurcation node is not detected in the previous intermediate image at the cross section A6, and a bifurcation node is still not detected in the current intermediate image at the cross section A7. Therefore, the processing control device 12 determines that the change of the bifurcation node indicates no change between cross sections A6 and A7, and does not update the event record according to the current intermediate image at the cross section A7 (step S905). In addition, if the processing control device 12 determines that the previous intermediate image and the current intermediate image both show the same bifurcation node, since the processing control device 12 already uses the bifurcation node in the previous intermediate image as the event node and records the corresponding event, the processing control device 12 may also regard the change of the bifurcation node as "no change", and performs step S905.

It should be noted that, the above described one or more embodiments performed based on the robotic bronchoscopy navigation system 1 of FIG. 1 may also be performed based on the robotic bronchoscopy navigation system 2 of FIG. 2, and the above described one or more embodiments performed based on the robotic bronchoscopy navigation system 2 of FIG. 2 may also be performed based on the robotic bronchoscopy navigation system 1 of FIG. 1.

In view of the above description, the robotic bronchoscopy navigation method and system according to one or more embodiments of the present disclosure, even if the preoperative medical image is different from the actual image during surgery or examination, the event-triggered navigation technology of the present disclosure may alleviate the need to obtain a precise bronchial model, and the moving direction of the bending part of the robotic bronchoscopy may be determined and adjusted in real time. Therefore, the robotic navigation system only needs to follow the sequence of events in the event record to make optimal movements in the actual body conduits (eg, bronchus).

What is claimed is:

1. A robotic bronchoscopy navigation system, comprising:

a robotic arm configured to control a robotic bronchoscopy; and a processing control device connected to the robotic arm to control the robotic bronchoscopy through the robotic arm, wherein the processing control device is configured to:

obtaining a navigation image, and performing a navigation procedure according to the navigation image, the navigation procedure comprising:

determining whether the navigation image has a node;

if the navigation image does not have the node, controlling a bending part of the robotic bronchoscopy to move toward an image center of the navigation image;

if the navigation image has the node, calculating a distance between the robotic bronchoscopy and the node; and controlling the bending part to move according to a default branch when the distance is smaller than a threshold of distance wherein the default branch is generated by identifying a change of a bifurcation node between a previous image and a current image taken by the robotic bronchoscopy during a path planning procedure, and is recorded in an event record where a node index is added by 1 when the bifurcation node does not exist in the previous image and exists in the current image;

wherein the processing control device performing controlling the bending part to move according to the default branch comprises:

calculating a virtual attraction force according to: (i) a virtual vector of the bending part relative to the image center, (ii) a speed obtained by performing first order differentiation on the virtual vector, (iii) an acceleration obtained by performing second order differentiation on the virtual vector, and (iv) a first distance between the bending part and the image center;

calculating a virtual repulsive force according to the virtual vector, the speed, the acceleration and a second distance between the bending part and an inner wall of the default branch; and controlling the robotic arm to control the bending part according to the virtual attraction force and the virtual repulsive force based on a controlling standard, wherein the controlling standard is to make the virtual vector approach zero.

2. The robotic bronchoscopy navigation system according to claim 1, wherein the processing control device is further configured to perform:

controlling the bending part to move a default distance toward the node;

determining whether the distance between the bending part and the node is smaller than the threshold of distance; and when the distance between the bending part and the node is not smaller than the threshold of distance, controlling the bending part to move according to a current movement direction.

3. The robotic bronchoscopy navigation system according to claim 2, wherein the processing control device performing controlling the bending part to move the default distance toward the node comprises:

calculating a vector of the node relative to the image center; and controlling the bending part to move toward the node according to the vector, for the node to be aligned with the image center.

4. The robotic bronchoscopy navigation system according to claim 1, wherein the processing control device performing calculating the virtual attraction force comprises: calculating the virtual attraction force based on the virtual vector, a generation coefficient and the first distance; and the processing control device performing calculating the virtual repulsive force comprises: using a distance between the bending part and a virtual inner wall as the second distance, and calculating the virtual repulsive force based on the virtual vector, another generation coefficient and the second distance, wherein a diameter of the virtual inner wall is smaller than a diameter of the default branch.

5. The robotic bronchoscopy navigation system according to claim 1, further comprising a horizontal level measuring mechanism provided on the robotic bronchoscopy, a horizontal level measurement index of the horizontal level measuring mechanism is presented on the navigation image, and before determining whether the navigation image has the node, the processing control device is further configured to control a direction of the bending part according to the horizontal level measurement index, for the horizontal level measurement index to represent a horizontal state.

* * * * *